US00RE40259E

(19) United States
(12) Reissued Patent
Pevarello et al.

(10) Patent Number: US RE40,259 E
(45) Date of Reissued Patent: *Apr. 22, 2008

(54) ALPHA-AMINOAMIDE DERIVATIVES USEFUL AS ANALGESIC AGENTS

(75) Inventors: Paolo Pevarello, Madrid (ES); Mario Varasi, Milan (IT); Patricia Salvati, Arese (IT); Claes Post, Sigtuna (SE)

(73) Assignee: Newron Pharmaceuticals, S.p.A., Milan (IT)

( * ) Notice: This patent is subject to a terminal disclaimer.

(21) Appl. No.: 11/359,982

(22) PCT Filed: Dec. 12, 1998

(86) PCT No.: PCT/EP98/08157

§ 371 (c)(1),
(2), (4) Date: Aug. 29, 2000

(87) PCT Pub. No.: WO99/35125

PCT Pub. Date: Jul. 15, 1999

Related U.S. Patent Documents

Reissue of:
(64) Patent No.: 6,306,903
Issued: Oct. 23, 2001
Appl. No.: 09/582,198
Filed: Aug. 29, 2000

(30) Foreign Application Priority Data

Dec. 31, 1997 (GB) ..... 9727523

(51) Int. Cl.
*A61K 31/275* (2006.01)
*A61K 31/165* (2006.01)
*C07C 255/50* (2006.01)
*C07C 233/05* (2006.01)

(52) U.S. Cl. ..... 514/522; 514/619; 514/620; 558/414; 564/163; 564/164; 564/171

(58) Field of Classification Search ..... 514/522, 514/619, 620; 558/414; 564/163, 164, 171
See application file for complete search history.

(56) References Cited

U.S. PATENT DOCUMENTS

| | | | | |
|---|---|---|---|---|
| 3,549,690 | A | | 12/1970 | Leigh et al. |
| 3,576,864 | A | | 4/1971 | Nagarajan |
| 3,658,967 | A | | 4/1972 | Leigh et al. |
| 4,049,663 | A | * | 9/1977 | Harper et al. ..... 546/233 |
| 4,267,354 | A | | 5/1981 | Krapcho et al. |

(Continued)

FOREIGN PATENT DOCUMENTS

| | | | | |
|---|---|---|---|---|
| EP | 0200101 | A2 | | 12/1986 |
| EP | 0415413 | A1 | | 3/1991 |
| EP | 0 525 360 | A | | 2/1993 |
| EP | 0 525 360 | A2 | | 2/1993 |
| GB | 1140748 | | | 1/1969 |
| GB | 2059963 | A | | 4/1981 |
| WO | WO 90/14334 | | | 11/1990 |
| WO | WO 94/22808 | | | 10/1994 |
| WO | WO 94/22809 | | | 10/1994 |
| WO | WO 96/40628 | | | 12/1996 |
| WO | WO 97/05102 | | * | 2/1997 |
| WO | WO 97/05111 | | | 2/1997 |
| WO | WO 98/19998 | | | 5/1998 |
| WO | WO 98/43964 | | | 10/1998 |
| WO | WO 98/47869 | | | 10/1998 |
| WO | WO 99/26614 | | | 6/1999 |
| WO | WO 99/39712 | | | 8/1999 |

OTHER PUBLICATIONS

New Riverside University Dictionary, The Riverside Publishing Company, Copyright 1984, 1988 and 1994, p. 845.*
Route of administration [online], [retrieved on Jun. 20, 2007]. Retrieved from the Internet, URL<http://en.wikipedia.org/w/index.php?title–Route_of_administration&oldid=139095793>.*
CDER Data Standards Manual [online], [retrieved on Jun. 20, 2007]. Retrieved from the Internet, URL <http://www.fda.gov/cder/dsm/DRG/drg00301.htm>.*

(Continued)

*Primary Examiner*—Rebecca Anderson
(74) *Attorney, Agent, or Firm*—Dechert, LLP

(57) ABSTRACT

The present invention relates to novel and known alpha-aminoamide compounds, to a process for their preparation, to pharmaceutical composition containing them and to their use as therapeutic agents.

In particular, the compounds of the present invention are endowed with analgesic properties and are particularly useful for the treatment and alleviation of chronic and neuropathic pain.

Accordingly, one object of the present invention is to provide the use of a compound of formula (I)

(I)

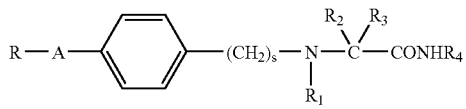

wherein:

A is a —$(CH_2)_m$—, —$(CH_2)_n$—X— or —$(CH_2)_v$—O— group wherein m is an integer of 1 to 4, n is zero or an integer of 1 to 4, X is —S— or —NH—, and v is zero or an integer of 1 to 5;

s is 1 or 2;

R is a furyl, thienyl, or pyridyl ring or a phenyl ring optionally substituted by one or two substituents independently chosen from halogen, cyano, $C_1$-$C_4$ alkyl, $C_1$-$C_4$ alkoxy and trifluoromethyl;

$R_1$ is hydrogen or $C_1$-$C_4$ alkyl;

one of $R_2$ and $R_3$ is hydrogen and the other is hydrogen or $C_1$-$C_4$ alkyl optionally substituted by hydroxy or phenyl; or $R_2$ and $R_3$ taken together with the carbon atom to which they are linked form a $C_3$-$C_6$ cycloalkyl ring; or $R_2$ and $R_3$ are both methyl;

$R_4$ is hydrogen or $C_1$-$C_4$ alkyl.

112 Claims, No Drawings

U.S. PATENT DOCUMENTS

| | | | | | |
|---|---|---|---|---|---|
| 4,311,853 | A | | 1/1982 | Cree et al. | |
| 4,513,009 | A | | 4/1985 | Roques et al. | |
| 4,631,287 | A | | 12/1986 | Chakraborty et al. | |
| 4,639,468 | A | | 1/1987 | Roncucci et al. | |
| 4,725,608 | A | | 2/1988 | Nakaguchi et al. | |
| 4,725,619 | A | | 2/1988 | Chakraborty et al. | |
| 4,839,369 | A | | 6/1989 | Youssefyeh et al. | |
| 4,927,835 | A | | 5/1990 | Kise et al. | |
| 4,927,836 | A | | 5/1990 | Holloway et al. | |
| 5,236,957 | A | * | 8/1993 | Dostert et al. | 514/620 |
| 5,391,577 | A | * | 2/1995 | Dostert et al. | 514/620 |
| 5,446,066 | A | * | 8/1995 | Varasi et al. | 514/620 |
| 5,449,692 | A | * | 9/1995 | Varasi et al. | 514/620 |
| 5,475,007 | A | | 12/1995 | Cai et al. | |
| 5,482,964 | A | | 1/1996 | Hays | |
| 5,498,610 | A | | 3/1996 | Chenard | |
| 5,502,079 | A | * | 3/1996 | Dostert et al. | 514/620 |
| 5,670,546 | A | | 9/1997 | Park et al. | |
| 5,688,830 | A | | 11/1997 | Berger et al. | |
| 5,723,489 | A | | 3/1998 | Sher et al. | |
| 5,741,818 | A | | 4/1998 | Dimmock | |
| 5,849,737 | A | | 12/1998 | Chaplan et al. | |
| 5,945,454 | A | | 8/1999 | Paverello et al. | 514/620 |
| 6,281,211 | B1 | | 8/2001 | Cai et al. | |
| 6,303,819 | B1 | * | 10/2001 | Pevarello et al. | 564/165 |
| 6,479,484 | B1 | | 11/2002 | Lan et al. | |
| 6,500,825 | B2 | | 12/2002 | Lan et al. | |
| 7,091,210 | B2 | | 8/2006 | Lan et al. | |
| 2004/0248978 | A1 | | 12/2004 | Salvati | |
| 2006/0079570 | A1 | | 4/2006 | Salvati et al. | |
| 2007/0093495 | A1 | | 4/2007 | Ruggero et al. | |
| 2007/0203182 | A1 | | 8/2007 | Besana et al. | |

OTHER PUBLICATIONS

Fariello et al., "Preclinical evaluation of PNU–151774E as a novel anticonvulsant," *J. Pharmacol. Exp. Ther.* 285(2):397–403 (May 1998).

Awouters (ed.), *Proceedings, XIVth International Symposium on Medicinal Chemistry, Maastricht, The Netherlands, Sep. 8–12, 1996,* Elsevier Science B.V. (Amsterdam), (cover, front matter, table of contents, index of authors, subject index, Stanford University Libraries date stamp). Copyright 1997; date stamped Aug. 24, 1998, Swain Library, Stanford University.

Vaghi et al., "Neuroprotective effect of PNU–151774E, a new anticonvulsant compound, in the model of global ischaemia in gerbils," from *Abstracts, Society for Neuroscience, 27th Annual Meeting, New Orleans, LA, Oct. 25–30, 1997.* (3 pages) (date stamped Apr. 26, 1999).

Elrifi et al., "Request for ex parte reexamination of U.S. Patent No. 6,479,484 B1," filed Jul. 2, 2003.

Webber, "Observations under article 115 EPC", filed Nov. 19, 2002 in EP 98958114.5 (EP 1032377).

Pevarello et al., "Stereoselectivity, sigma binding and sodium channel blocking activity of 2–aminopropanamide anticonvulsants," from *Abstracts, XIVth International Symposium on Medicinal Chemistry, Maastricht, the Netherlands, Sep. 8–12, 1996* (4 pages) (Sep. 8, 1996).

Pevarello et al., "Stereoselectivity, sigma binding and sodium channel blocking activity of 2–amino propanamide anticonvulsants." (3 pages) (Sep. 12, 1996).

Salvati et al., "Anticonvulsant profile of FCE 26743A, a novel 2–aminopropionamide derivative," #825.16, from *Abstracts, Society for Neuroscience 26th Annual Meeting, Washington DC, Nov. 16–21, 1996,* (2 pages) (Nov. 16, 1996, date solely for purpose of initial consideration).

Salvati et al., "Anticonvulsant profile of FCE 26743A, a novel 2–aminopropionamide derivative," #825.16, from *Abstracts, Society for Neuroscience 26th Annual Meeting, Washington DC, Nov. 16–21, 1996.* (3 pages) (Nov. 16, 1996, date solely for purpose of initial consideration).

Salvati et al., "Anticonvulsant profile of FCE26743A (PNU–151774), a novel 2–aminopropionamide derivative. Society for Neuroscience. Washington. Nov. 15–21, 1996." (4 pages) (Nov. 21, 1996, date solely for purpose of initial consideration).

Vaghi et al., "Neuroprotective effect of PNU–151774E, a new anticonvulsant compound, in the model of global ischaemia in gerbils," from *Abstracts, Society for Neuroscience 27th Annual Meeting, New Orleans, LA, Oct. 25–30, 1997,* (2 pages) (Oct. 25, 1997, date solely for purpose of initial consideration).

Vaghi et al., "Neuroprotective effect of PNU–151774E, a new anticonvulsant compound, in the model of global ischaemia in gerbils." (5 pages) (Oct. 30, 1997, date solely for purpose of initial consideration).

Cover and bibliographic page, from *Abstracts, Society for Neuroscience 26th Annual Meeting, Washington DC, Nov. 16–21, 1996,* (2 pages) (Nov. 16, 1996, date solely for purpose of initial consideration).

Varasi et al., "Synthesis and anticonvulsant activity of new benzyloxybenzylacetamide derivatives," from *Abtracts, XIIth International Symposium on Medicinal Chemistry, Basel, Switzerland, Sep. 13–17, 1992* (2 pages) (1992).

Varasi et al., "Synthesis and anticonvulsant activity of new benzyloxybenzylacetamide derivatives" (2 pages) (1992).

Anonymous, "Neurogen Licenses National Institutes of Health (NIH) anticonvulsants," *SCRIP World Pharmaceutical News* 1773:14 (1992).

Anonymous, "Cambridge NeuroScience's grant for channel blockers," *SCRIP World Pharmaceutical News* 1870:8 (1993).

Bensimon, G., et al., "A Controlled Trial of Riluzole in Amyotrophic Lateral Sclerosis," *New Engl. J. Med.* 330:585–591 (1994).

Brown, C.M., et al., "Neuroprotective properties of Lifarizine compared with those of other agents in a mouse model of focal cerebral ischaemia," *British J. Pharmacol.* 115:1425–1432 (1995).

Catterall, W.A., "Common modes of drug action on $Na^+$ channels: Local anesthetics, antiarrhythmics and anticonvulsants," *Trends Pharmacol. Sci.* 8:57–65 (1987).

Catterall, W.A., "Neurotoxins that Act on Voltage–Sensitive Sodium Channels in Excitable Membranes," *Ann. Rev. Pharmacol. Toxicol.* 20:15–43 (1980).

Catterall, W.A., "Structure and Function of Voltage–Sensitive Ion Channels," *Science* 242:50–61 (1988).

Denicoff, K.D., et al., "Efficacy of Carbamazepine Compared With Other Agents: A Clinical Practice Survey," *J. Clin. Psychiatry* 55:70–76 (1994).

Dimmock, J.R., et al., "(Aryloxy)aryl Semicarbazones and Related Compounds: A Novel Class of Anticonvulsant Agents Possessing High Activity in the Maximal Electroshock Screen," *J. Med. Chem.* 39:3984–3997 (1996).

Graham, S.H., et al., "Neuroprotective Effects of a Use–Dependent Blocker of Voltage–Dependent Sodium Channels, BW619C89, in Rat Middle Cerebral Artery Occlusion," *J. Pharmacol. Exp. Ther.* 269:854–859 (1994).

Stys, P.K., et al., "Ionic Mechanism of Anoxic Injury in Mammalian CNS White Matter: Role of $Na_+$ Channels and $Na^+$–$Ca^{2+}$ Exchanger," *J. Neurosci.* 12:430–439 (1992).
Taylor, C.P. and Meldrum, B.S., "$Na^+$ channels as targets for neuroprotective drugs," *Trends Pharmacol. Sci.* 16:309–316 (1995).
Fields, "Peripheral neuropathic pain: an approach to management," in PD Wall and R Melack (eds.), *Textbook of Pain,* $3^{rd}$ ed., Churchill Livingstone, pp. 991–996 (1994).
Galer, BS, "Neuropathic pain of peripheral origin: advances in pharmacologic treatment," *Neurol.* 45:S17–S25, 1995.
Lunardi et al., "Clinical effectiveness of lamotrigine and plasma levels in essential and symptomatic trigeminal neuralgia," *Neurology* 48(6):1714–1717 (1997).
Nakamura–Craig et al., "Effect of lamotrigine in the acute and chronic hyperalgesia induced by $PGE_2$ and in the chronic hyperalgesia in rats with streptozocin–induced diabetes," *Pain* 63:33–37 (1995).
Tanelian et al., "Neuropathic pain can be relieved by drugs that are use–dependent sodium channel blockers: lidocaine, carbamazepine, and mexiletine," *Anesthesiol.* 74(5):949–951 (1991).
Wilton, "Tegretol in the treatment of diabetic neuropathy," S. Afr. Med. J. 48(20):869–872 (1974).
Woolf et al., "The systemic administration of local anaesthetics produces a selective depression of C–afferent fibre evoked activity in the spinal cord," *Pain* 23(4):361–374 (1985).
Hammer et al., "Effect of Riluzole on acute pain and hyperalgesia in humans," *Brit. J. Anaesthesia* 82(5):718–22 (1999).
Tanelian et al., "Sodium channel–blocking agents: their use in neuropathic pain conditions," *Pain Forum* 4(2):75–80 (1995).
Shibata et al., "Modified formalin test: characteristic biphasic pain response," *Pain* 38:347–352 (1989).
Tjolsen et al., "The formalin test: an evaluation of the method," *Pain* 51:5–17 (1992).
Judgment, Preliminary Motions, Bd.R. 127, interference No. 105,394 (2007).
Decision, Preliminary Motions, Bd.R. 125, interference No. 105,394 (2007).
Memorandum Opinion and Order, interference No. 105,394 (2007).
Puig et al., "Formalin–evoked activity in identified primary afferent fibers: systemic lidocaine suppresses phase–2 activity," *Pain* 64:345–355 (1995).
First Declaration of Stephen G. Waxman, M.D., Ph.D., PX 2003, interference No. 105,394 (2006).
"Synthesis and Anticonvulsant Activity of a New Class of 2—(Arylalky) aminolalkanamide Derivatives", Pevarello et al, *Journal of Medicinal Chemistry*, vol. 41, No. 4, Feb. 12, 1998, pp. 579–590.
Pevarello et al., "Synthesis and Anticonvulsant Activity of a New Class of 2–[(Arylalkyl)amino]alkanide Derivatives", J. Med. Chem. 41:579–590 (1998).
(First) Declaration of Robert A. McArthur, Pevarello Exhibit 2036, interference 105,394 (2006).
Vieth et al., "Characteristic Physical Properties and Structural Fragments of Marketed Oral Drugs," *J. Med. Chem.* 47:224–232 (2004).
Supplemental data, Vieth et al., "Characteristic Physical Properties and Structural Fragments of Marketed Oral Drugs," *J. Med. Chem.* 47:224–232 (2004) (downloaded Aug. 20, 2007 from http://pubs.acs.org) (excerpted fields).
Complaint, Civil Action No. 1:07–cv–00487 (Mar. 12, 2007).
Notice Of Dismissal With Prejudice, Civil Action No. 1:07–cv–00487 (Jul. 25, 2007).
Dostert et al., "New anticonvulsants with selective MAO–B inhibitory activity," *European Neuropsychopharmacology,* 1(3):317–319 (Sep. 1991).
Specification and claims as amended by preliminary amendment, U.S. Appl. No. 10/569,403 (pending).
Specification and claims as amended by preliminary amendment, U.S. Appl. No. 10/586,494 (pending).
Specification and claims as amended by (first) and second preliminary amendments, U.S. Appl. No. 11/574,751.
Official action, counterpart Brazilian application No. PI 9814548–7 (translation).
Kingery, "A critical review of controlled clinical trials for peripheral neuropathic pain and complex regional pain syndromes," *Pain* 73:123–139 (1997).
Guieu et al., "Central analgesic effect of valproate in patients with epilepsy," *Seizure* 2:147–150 (1993).
McQuay et al., "Anticonvulsant drugs for management of pain: a systematic review," *BMJ* 311:1047–1052 (Oct. 21, 1995).

* cited by examiner

ALPHA-AMINOAMIDE DERIVATIVES USEFUL AS ANALGESIC AGENTS

Matter enclosed in heavy brackets [ ] appears in the original patent but forms no part of this reissue specification; matter printed in italics indicates the additions made by reissue.

This appln is a 371 of PCT/EP98/08157 filed Dec. 12, 1998.

The present invention relates to novel and known alpha-aminoamide compounds, to a process for their preparation, to pharmaceutical composition containing them and to their use as therapeutic agents.

In particular, the compounds of the present invention are endowed with analgesic properties and are particularly useful for the treatment and alleviation of chronic and neuropathic pain.

Chronic and neuropathic pain are associated with prolonged tissue damage or injuries to the peripheral or central nervous system and result from a number of complex changes in nociceptive pathways.

Clinical manifestations of chronic pain include a sensation of burning or electric shock, feelings of bodily distortion, allodynia and hyperpathia.

Despite the large number of available analgesics, their use is limited by severe side effects and modest activity in some pain conditions. Therefore there is still a clear need to develop new compounds.

International applications WO 90/14334, WO 94/22808, WO 97/05111 and WO 97/05102 disclose substituted benzylaminopropionamide compounds active on the central nervous system and useful as anti-epileptic, anti-Parkinson, neuroprotective, antidepressant, antispastic and hypnotic agents.

The present invention is based on the finding that compounds known from the above-cited international applications and new ones, closely related thereto, have analgesic properties in mammals, including humans.

Accordingly, one object of the present invention is to provide the use of a compound of formula (I)

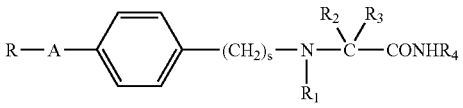

(I)

wherein:

A is a $—(CH_2)_m—$, $—(CH_2)_n—X—$ or $—(CH_2)_v—O—$ group wherein m is an integer of 1 to 4, n is zero or an integer of 1 to 4, X is —S— or —NH—, and v is zero or an integer of 1 to 5;

s is 1 or 2;

R is a furyl, thienyl, or pyridyl ring or a phenyl ring optionally substituted by one or two substituents independently chosen from halogen, cyano, $C_1$-$C_4$ alkyl, $C_1$-$C_4$ alkoxy and trifluoromethyl;

$R_1$ is hydrogen or $C_1$-$C_4$ alkyl;

one of $R_2$ and $R_3$ is hydrogen and the other is hydrogen or $C_1$-$C_4$ alkyl optionally substituted by hydroxy or phenyl; or $R_2$ and $R_3$ taken together with the carbon atom to which they are linked form a $C_3$-$C_6$ cycloalkyl ring; or $R_2$ and $R_3$ are both methyl;

$R_4$ is hydrogen or $C_1$-$C_4$ alkyl;

or a pharmaceutically acceptable salt thereof;

and wherein when A is a $—(CH_2)_5—O—$ group then s is 1, R is a phenyl group optionally substituted by one or two substituents selected independently from halogen, trifluoromethyl and $C_3$-$C_4$ alkoxy, $R_1$ is hydrogen and one of $R_2$ and $R_3$ is hydrogen and the other is hydrogen or $C_1$-$C_4$ alkyl optionally substituted hydroxy;

and wherein when $R_2$ and $R_3$ are both methyl then R is other than furyl, thienyl or pyridyl ring, in the manufacture of a medicament for use as analgesic, in particular for the treatment and alleviation of chronic and neuropathic pain.

A $—(CH_2)_m—$, $—(CH_2)_n—$ or $—(CH_2)_v—$ chain may be a branched or straight chain. Alkyl and alkoxy groups may be branched or straight groups. Representative examples of $C_1$-$C_4$ alkyl groups include methyl, ethyl, n- and iso-propyl, n-, iso- sec- and tert-butyl.

Representative examples of $C_1$-$C_4$ alkoxy groups include methoxy and ethoxy.

A $C_3$-$C_6$ cycloalkyl group is for instance cyclopropyl, cyclopentyl or cyclohexyl, in particular cyclopentyl or cyclohexyl.

A halogen atom is fluorine, bromine, chlorine or iodine, in particular, chlorine or fluorine.

Pharmaceutically acceptable salts of the compounds of the invention include acid addition salts with inorganic, e.g. nitric, hydrochloric, hydrobromic, sulphuric, perchloric and phosphoric acids or organic, e.g. acetic, trifluoroacetic, propionic, glycolic, lactic, oxalic, malonic, malic, maleic, tartaric, citric, benzoic, cinnamic, mandelic and salicylic acids.

The compounds of formula (I) have asymmetric carbon atoms and therefore they can exist either as racemic mixtures or as individual optical isomers (enantiomers).

Accordingly, the present invention also include within its scope all the possible isomers and their mixtures and both the metabolites and the pharmaceutically acceptable bioprecursors (otherwise known as pro-drugs) of the compounds of formula (I).

Preferred compounds of formula (I) are those wherein

A is a group chosen from $—CH_2—$, $—CH_2—CH_2—$, $—CH_2—S—$, $—CH_2—CH_2—S—$ and $—(CH_2)_v—O—$ in which v is an integer of 1 to 5;

s is 1 or 2;

R is a phenyl ring optionally substituted by one or two substituents independently chosen from halogen and cyano or a thienyl ring;

$R_1$ is hydrogen or $C_1$-$C_4$ alkyl;

one of $R_2$ and $R_3$ is hydrogen and the other is $C_1$-$C_4$ alkyl optionally substituted by hydroxy or phenyl; or $R_2$ and $R_3$ are both methyl;

$R_4$ is hydrogen or $C_1$-$C_4$ alkyl; and the pharmaceutically acceptable salts thereof.

Examples of specific compounds of formula (I) are:

2-[4-(3-fluorobenzyloxy)benzylamino]-2-methylpropanamide;

2-[4-(3-fluorobenzyloxy)benzylamino]propanamide;

2-([4-benzyloxybenzylamino)propanamide;

2-[4-(2-fluorobenzyloxy)benzylamino]propanamide;

2-[4-(4-fluorobenzyloxy)benzylamino]propanamide;

2-[4-(2-chlorobenzyloxy)benzylamino]propanamide;

2-(4-(3-chlorobenzyloxy)benzylamino]propanamide;

2-[4-(3-fluorobenzyloxy)benzylamino]-3-hydroxy-N-methylpropanamide;

2-[4-(2-fluorobenzyloxy)benzylamino]-3-hydroxy-N-methylpropanamide;

2-[4-(2-chlorobenzyloxy)benzylamino]-3-hydroxy-N-methylpropanamide;

2-[4-(3-cyanobenzyloxy)benzylamino]-3-hydroxy-N-methylpropanamide;

2-[4-(3-chlorobenzyloxy)phenylethylamino]-propanamide;

2-(4-benzyloxybenzylamino)-3-hydroxy-N-methylpropanamide;

2-(4-(2-thenyloxy)benzylamino)-propanamide;

2-[4-(3-fluorobenzyloxy)benzylamino]-N-methylpropanamide;

2-[4-(3-fluorobenzyloxy)benzylamino]-3-hydroxypropanamide;

2-[4-(2-(3-fluorophenyl)ethyloxy)benzylamino]-propanamide;

2-[4-(2-(3-fluorophenyl)ethyl)benzylamino]-propanamide;

2-[N-4-benzyloxybenzyl-N-methyl-amino]-propanamide;

2-[2-(4-(3-chlorobenzyloxy)phenylethyl)amino]-propanamide;

2-[4-benzylthiobenzylamino]-propanamide;

2-[4-(3-phenylpropyloxy)benzylamino]-propanamide;

2-[4-(4-phenylbutyloxy)benzylamino]-propanamide;

2-[4-(5-phenylpentyloxy)benzylamino]-propanamide;

2-[4-benzyloxybenzylamino]-3-phenyl-N-methylpropanamide;

2-[4-benzyloxybenzylamino]-3-methyl-N-methylbutanamide, if the case either as a single isomer or as a mixture thereof, and the pharmaceutically acceptable salts thereof.

An aspect of this invention relates to a pharmaceutically composition having analgesic activity, in particular against chronic and neuropathic pain, comprising a compound of formula (I), as herein defined, as an active agent and a pharmaceutically acceptable salt thereof.

A further aspect of this invention relates to a method of treating a mammal, including humans, in need of an analgesic agent, said method comprising administering thereto an effective amount of a compound of formula (I) or a pharmaceutically acceptable salt thereof.

Neuropathic and chronic pain conditions in a mammal can thus be alleviated and treated. Examples of pain conditions that can be treated by a compound of formula (I) include:

peripheral neuropathies, such as trigeminal neuralgia, postherapeutic neuralgia, diabetic neuropathy, glossopharyngeal neuralgia, radiculopathy, and neuropathy secondary to metastatic infiltration, adiposis dolorosa and burn pain; and central pain conditions following stroke, thalamic lesions and multiple sclerosis. "Treatment" as used herein covers any treatment of a condition in a mammal, particularly a human, and includes:

(i) preventing the disease from occurring in a subject which may be predisposed to the disease, but has not yet been diagnosed as having it;

(ii) inhibiting the condition, i.e., arresting its development; or (iii) relieving the condition, i.e., causing regression of the disease.

Another object of the present invention are the novel compounds of formula (IA)

(IA)

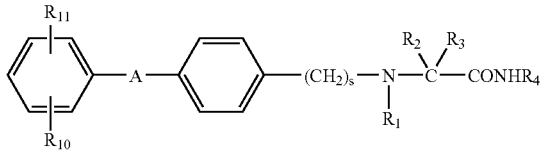

wherein:

A is a —$(CH_2)_m$— or —$(CH_2)_n$—E— group wherein m is an integer of 1 to 4, n is zero or an integer of 1 to 4 and E is —O—, —S— or —NH—;

s is 1 or 2;

one of $R_{10}$ and $R_{11}$ is cyano and the other is independently selected from hydrogen, halogen, cyano, $C_1$-$C_4$ alkyl, $C_1$-$C_4$ alkoxy and trifluoromethyl;

$R_1$ is hydrogen or $C_1$-$C_4$ alkyl;

one of $R_2$ and $R_3$ is hydrogen and the other is hydrogen or $C_1$-$C_4$ alkyl optionally substituted by hydroxy or phenyl; or $R_2$ and $R_3$ taken together with the carbon atom to which they are linked form a $C_3$-$C_6$ cycloalkyl ring; or $R_2$ and $R_3$ are both methyl;

$R_4$ is hydrogen or $C_1$-$C_4$ alkyl; and the pharmaceutically acceptable salts.

The compounds of formula (IA) fall within the scope fo the compound of formula (I), as herein defined. Therefore all the definitions and biological properties stated above as to a compound of formula (I) apply also to a compound of formula (IA).

In particular, preferred compounds of formula (IA) are those wherein

A is a group —$CH_2$—O— or —$CH_2$—$CH_2$—O—, s is 1;

one of $R_{10}$ and $R_{11}$ is cyano and the other is hydrogen, cyano or halogen; and one of $R_2$ and $R_3$ is hydrogen and the other is $C_1$-$C_4$ alkyl optionally substituted by hydroxy; or $R_2$ and $R_3$ are both methyl and the pharmaceutically acceptable salts thereof.

Specific examples of compounds of formula (IA) are:

2-[4-(3-cyanobenzyloxy)benzylamino]-3-hydroxy-N-methylpropanamide;

[2-[4-(3-cyanobenzyloxy)benzyl]-2-methyl-amino]-3-hydroxy-N-methyl-propanamide, if the case either as a single isomer or as a mixture thereof, and the pharmaceutically acceptable salts thereof.

The compounds of formula (I) and (IA) and the pharmaceutically acceptable salts thereof can be obtained by well known processes as described in the above cited international applications. In particular, a compound of formula (IA) and the salts thereof can be obtained by a process comprising:

a) reacting a compound of formula (II)

(II)

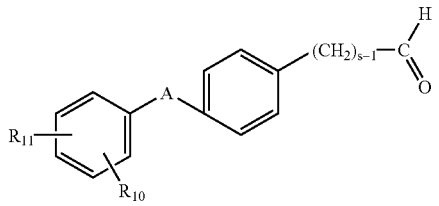

wherein $R_{10}$, $R_{11}$, A and s are as defined above, with a compound of formula (III)

(III)

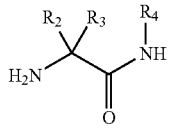

wherein $R_2$, $R_3$ and $R_4$ are as defined above, in the presence of a reducing agent thus obtaining a compound of formula (IA) in which $R_1$ is hydrogen; or b) reacting a compound of formula (IV)

(IV)

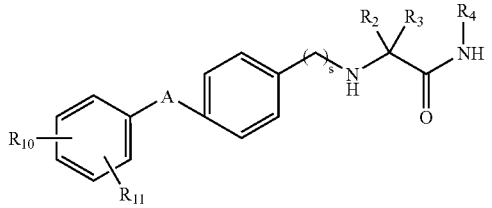

wherein $R_2$, $R_3$, $R_4$, $R_{10}$, $R_{11}$, A and s are as defined above, with a compound of formula (V) or (VI) in this latter case in the presence of a reducing agent $$R'_5W \quad (V)$$

$$R''_5CHO \quad (VI)$$

wherein W is a halogen atom; $R'_5$ is $C_1$-$C_4$ alkyl and $R''_5$ is hydrogen or $C_1$-$C_3$ alkyl, thus obtaining a compound of formula (IA) in which $R_1$ is $C_1$-$C_4$ alkyl; and, if desired, converting a compound of formula (IA) into another compound of formula (IA) and/or, if desired, converting a compound of formula (IA) into a pharmaceutically acceptable salt and/or, if desired, converting a slat into a free compound.

All the processes described hereabove are analogy processes and can be carried out according to well known methods in organic chemistry.

A compound of formula (IV) is a compound of formula (IA) in which $R_1$ is hydrogen.

The reaction of a compound of formula (II) with a compound of formula (III) to give a compound of formula (IA) or (IV) is a reductive amination reaction which can be carried out according to well known methods. According to a preferred embodiment of the invention it may be performed under nitrogen atmosphere, in a suitable organic solvent, such as an alcohol, e.g. a lower alkanol, in particular methanol, or in acetonitrile, at a temperature ranging from about 0° C. to about 40° C., in the presence of a reducing agent, the most appropriate being sodium cyanoborohydride.

Occasionally molecular sieves can be added to the reaction mixture for facilitating the reaction.

In a compound of formula (V) the halogen W is preferably iodine. The alkylation reaction of a compound of formula (IV) with a compound of formula (V) can be carried out in a suitable organic solvent, such as an alcohol, e.g. methanol, ethanol or isopropanol, in particular in ethanol, at a temperature ranging from about 0° C. to about 50° C.

The alkylation reaction of a compound of formula (IV) with an aldehyde of formula (VI) can be carried out in a suitable organic solvent, such as an alcohol, e.g. methanol, ethanol or acetonitrile in the presence of a suitable reducing agent, such as sodium cyanoborohydride, at a temperature ranging from about 0° C. to about 30° C.

A compound of formula (IA) can be converted, as stated above, into another compound of formula (IA) by known methods. Process-variant b) above may be regarded as an example of optional conversion of a compound of formula (IA) into another compound of formula (IA).

Also the optional salification of a compound of formula (IA) as well as the conversion of a salt into the free compound may be carried out by conventional methods.

The compounds of formula (II) and (III), (V) and (VI) are known compounds or can be obtained by known methods. When in the compounds of the present invention and in the intermediate-products thereof, groups are present, which need to be protected before submitting them to the hereabove illustrated reactions, they may be protected before being reacted and then deprotected according to methods well known in organic chemistry.

The compounds of formula (I), (IA) and the pharmaceutically acceptable salts thereof are hereinafter defined as "the compounds of the invention" or "the active agents of the invention".

Pharmacology

As stated above, the compounds of the invention are active as analgesic agents, as proven for instance by the fact that they have been found to be active in the formalin test.

Formalin test is a useful tool for obtaining neurogenic inflammation and continuous pain (Shibata et al, Pain, 38: 347-352, 1989).

Formalin produces a distinct biphasic response. The early phase seems to be caused predominantly by C-fibre activation due to peripheral stimulus, while the late phase appears to be dependent on the combination of an inflammatory reaction in the peripheral tissue and functional changes in the dorsal horn of the spinal cord. This functional changes seem to be initiated by the C-fibre barrage during the early phase (Tjolsen et al. Pain 51, 5-17, 1992). Substance P and bradykinin participate in the early phase, while histamine, serotonin, prostaglandins and bradykinin are involved in the late phase.

Formalin Test

Male [NMRI] *CD-1* mice (22-25 g) were injected with 20 [ml] *μl* of 2.7% solution of formalin into the right hindpaw and placed immediately into observation chambers. The cumulative licking time of the injected paw was recorded in the acute phase (0-5 min) and in the chronic phase (30-40 min) of the nociceptive response of formalin.

The two representative compounds of the invention (S)-2-[4-(3- fluorobenzyloxy)benzylamino]-propanamide, methanesulfonate (internal code PNU 151774E) and [(S)-[2-[4-(3-fluorobenzyloxy)benzylamino]-2-methylpropanamide] *2-[4-(3-fluorobenzyloxy)benzylamino]-2-*

*methyl-propanamide* (internal code PNU 156654E) were administered 60 min before formalin injection at the doses of 7.5, 15.0, 30.0 and 60.0 mg/kg; po. Morphine (5 mg/kg; sc) was used as a positive standard. The activities data *were* analysed by Dunnett's t-test.

Locomotor Activity and Rotarod

The effects of these compounds on locomotor activity and rotarod (a test for evaluating motor co-ordination) were studied in order to exclude changes in these parameters as confounding factors in the evaluation of the formalin response. The locomotor activity test lasted 15 min. Five minutes after testing locomotor activity, the mice were put on the rotarod for 2 min and the number of mice falling within this time were counted.

Compounds PNU 151774E and PNU 156654E were tested at the doses of 7.5, 15.0, 30.0 and 60.0 mg/kg; po. The compounds were administered 60 min before locomotor activity test.

Results

Compounds PNU 151774E and PNU 156654E dose-dependently reduced cumulative licking time in both phases of the formalin test (Table 1) demonstrating analgesic activity without any effect on locomotor or rotarod activity (Table 2).

TABLE 1

Effects of PNU 151774E and PNU 156654E in the formalin nociception test in mice

| Compound | Dose (mg/kg; po) | Licking time (sec) Acute phase | Licking time (sec) Chronic phase |
|---|---|---|---|
| vehicle | 0.0 | 160.2 ± 2.6 | 74.8 ± 3.7 |
| PNU 151774E | 7.5 | 137.9 ± 2.4[a] | 72.4 ± 2.4 |
| | 15.0 | 87.9 ± 3.3[a] | 64.3 ± 2.8[b] |
| | 30.0 | 79.4 ± 3.0[a] | 56.9 ± 2.6[a] |
| | 60.0 | 63.1 ± 2.6[a] | 38.1 ± 3.6[a] |
| vehicle | 0.0 | 119.4 ± 5.2 | 73.1 ± 6.0 |
| PNU 156654E | 7.5 | 108.4 ± 4.2 | 62.4 ± 3.6 |
| | 15.0 | 79.7 ± 3.7[a] | 42.1 ± 6.2[a] |
| | 30.0 | 60.0 ± 2.3[a] | 37.7 ± 6.9[a] |
| | 60.0 | 44.4 ± 4.2[a] | 17.3 ± 6.6[a] |

[a]= $p < 0.01$;
[b]= $p < 0.05$

TABLE 2

Effects of PNU 151774E and PNU 156654E on locomotor activity and rotarod

| Compound | Dose (mg/kg; po) | Locomotor activity counts (mean ± sem) | Rotarod co-ordination (mice fallen/ total mice) |
|---|---|---|---|
| vehicle | 0 | 2653 ± 163 | 0/10 |
| PNU 151774E | 7.5 | 2908 ± 234 | 0/10 |
| | 15 | 2795 ± 255 | 0/10 |
| | 30 | 2347 ± 203 | 0/10 |
| | 60 | 2240 ± 195 | 0/10 |
| vehicle | 0 | 1976 ± 232 | 0/10 |
| PNU 156654E | 7.5 | 1966 ± 188 | 0/10 |
| | 15 | 2110 ± 256 | 0/10 |
| | 30 | 2272 ± 317 | 0/10 |
| | 60 | 2119 ± 310 | 0/10 |

In view of their biological activity, the compounds of the invention are useful in mammals, including humans, as analgesic agents. In particular they are useful in treating pain associated with damage or permanent alteration of the peripheral or central nervous system, for example peripheral neuropathies, such as trigeminal neuralgia, postherapeutic neuralgia, diabetic neuropathy, raticulopathy glossopharyngeal neuralgia, and neuropathy secondary to metastatic infiltration, adiposis dolorosa, and burn pain; and central pain conditions following stroke, thalamic lesions and multiple sclerosis.

The conditions of a patient in need of an analgesic agent may thus be improved.

The compounds of the invention can be administered in a variety of dosage forms, e.g. orally, in the form of tablets, capsules, sugar or film coated tablets, liquid solutions or suspensions; rectally in the form of suppositories; parenterally, e.g. intramuscularly, or by intravenous injection or infusion.

The dosage depends on the age, weight, conditions of the patient and on the administration route; for example, the dosage adopted for oral administration to adult humans e.g. for the representative compounds of the invention (S)-2-[4-(3-fluorobenzyloxy)benzylamino]-propanamide, methanesulfonate,

[(S)-[2-[4-(3-fluorobenzyloxy)benzylamino]-2-methyl-propanamide]

*2-[4-(3-fluorobenzyloxy)benzylamino]-2-methyl-propanamide*, and (S)-[2-[4-(3-cyanobenzyloxy)benzylamino]-3-hydroxy-N-methylpropanamide may range from about 1 to about 500 mg pro dose, from 1 to 5 times daily.

The invention includes pharmaceutical compositions comprising a compound of formula (IA), as an active principle, in association with a pharmaceutically acceptable excipient (which can be a carrier or a diluent). The pharmaceutical compositions containing the compounds of the invention are usually prepared following conventional methods and are administered in a pharmaceutically suitable form.

For example, the solid oral forms may contain, together with the active compound, diluents, e.g. lactose, destrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; desegregating agents, e.g. a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersion for oral administration may be e.g. syrups, emulsions and suspension.

The syrups may contain as carrier, for example, saccharose or saccharose with glycerine and/or mannitol and/or sorbitol.

The suspension and the emulsion may contain as carrier, for example, a natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusion may contain as carrier, for example, sterile water or preferably they may be in the form of sterile, aqueous, isotonic saline solutions.

The suppositories may contain together with the active compound a pharmaceutically acceptable carrier, e.g. cocoa butter, polyethylene glycol, a polyoxyethylene sorbitan fatty acid ester surfactant or lecithin.

The following examples illustrate but do not limit the invention.

EXAMPLE 1

(S)-2-[4-(3-cyanobenzyloxy)benzylamino]-3-hydroxy-N-methyl-propanamide

To a solution of N-methylserinamide hydrochloride (2 g; 0.0129 mol), in methanol (40 ml), 2 g of powdered 3A molecular sieves are added; after stirring 15' at room temperature, 0.65 g (0.0102 mol) of sodium cyanoborohydride are added in a single portion followed by 2.85 g (0.012 mol) of 4-(3-cyanobenzyloxy)benzaldehyde. The mixture is stirred for 2 hours at room temperature, then filtered and the residue after evaporation is separated by flash-chromatography on silica gel (eluant: chloroform 98: methanol 2: 30% NH4OH 0.2). 2.6 g (63%) of pure titled compound (m.p. 130-134° C.).

$[\alpha]_D$: +12.8 (c=1.25 AcOH)

EXAMPLE 2

(S)-[2-[4-(3-cyanobenzyloxy)benzyl]-2-methyl-amino]-3-hydroxy-N-methyl-propanamide (S)-2-[4-(3-cyanobenzyloxy)benzylamino]-3-hydroxy-N-methyl-propanamide (2 g; 0.0059 mol) is dissolved in methanol (30 ml) and 1.8 g (0.013 mol) of anhydrous potassium carbonate are added to the solution. Methyl iodide (1.5 ml; 0.025 mol) is dropped into the mixture which is stirred for 2 hours at room temperature and then evaporated to dryness. The crude residue is chromatographed on silica gel (eluant:chloroform/methanol; 95/5). 1.88 g (90%) of (S)-[2-[4-(3-cyanobenzyloxy)benzyl]-2-methyl-amino]-3-hydroxy-N-methyl-propanamide are obtained.

Elemental Analysis:

| Atom | Calc. | Found |
|---|---|---|
| C | 67.97 | 67.69 |
| H | 6.56 | 6.48 |
| N | 11.89 | 11.98 |

EXAMPLE 3

With the usual methods of pharmaceutical technique, preparation can be made of capsules having the following composition:

| | |
|---|---|
| (S)-2-[4-(3-cyanobenzyloxy)benzylamino]-3-hydroxy-N-methyl-propanamide | 50 mg |
| Talc | 2 mg |
| Corn starch | 2 mg |
| Microcristalline cellulose | 6 mg |
| Magnesium stearate | 1 mg |

What is claimed is:

1. A method of treating *acute or chronic* pain in a patient in need thereof, said method comprising administering to [the] *a* patient *in need of such treatment* a medicament comprising an *analgesically* effective amount of [an analgesic which is] an alpha-aminoamide compound of formula (I)

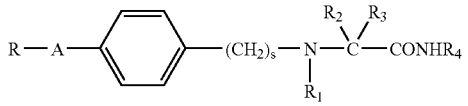

(I)

wherein:

A is a —$(CH_2)_m$—, —$(CH_2)_n$—X— or —$(CH_2)_v$—O— group wherein m is an integer of 1 to 4, n is zero or an integer of 1 to 4, X is —S— or —NH—, and v is zero or an integer of 1 to 5;

s is 1 or 2;

R is [a ring or] a phenyl ring optionally substituted by one or two substituents independently [chosen] *selected* from halogen, cyano, $C_1$-$C_4$ alkyl, $C_1$-$C_4$ alkoxy and trifluoromethyl;

$R_1$ is hydrogen or $C_1$-$C_4$ alkyl;

one of $R_2$ and $R_3$ is hydrogen and the other is hydrogen or $C_1$-$C_4$ alkyl optionally substituted by hydroxy or phenyl; or $R_2$ and $R_3$ taken together with the carbon atom to which they are linked form a $C_3$-$C_6$ cycloalkyl ring; or $R_2$ and $R_3$ are both methyl;

$R_4$ is hydrogen or $C_1$-$C_4$ alkyl;

or a pharmaceutically acceptable salt thereof;

with the proviso that[.] when A is a —$(CH_2)_5$—O— group then s is 1, R is a phenyl group optionally substituted by one or two substituents selected independently from halogen, trifluoromethyl and $C_1$-$C_4$ alkoxy, $R_1$ is hydrogen and one of $R_2$ and $R_3$ is hydrogen and the other is hydrogen or $C_1$-$C_4$ alkyl optionally substituted *by* hydroxy.

[2. A method of treating chronic or neuropathic pain in a patient in need thereof, said method comprising the method according to claim 1.]

3. The method according to claim 1 *or claim 6*, wherein in the compound of formula (I), A is a group [chosen] *selected* from —$CH_2$—, —$CH_2CH_2$—, —$CH_2$—S—, —$CH_2$—$CH_2$—S— and —$(CH_2)_v$—O— in which v is an integer of 1 to 5;

s is 1 or 2;

R is a phenyl ring optionally substituted by one or two substituents independently [chosen] *selected* from halogen and cyano [or a thienyl ring];

$R_1$ is hydrogen or $C_1$-$C_4$ alkyl; one of $R_2$ and $R_3$ is hydrogen and the other is $C_1$-$C_4$ alkyl optionally substituted by hydroxy or phenyl; or $R_2$ and $R_3$ are both methyl; and $R_4$ is hydrogen or $C_1$-$C_4$ alkyl.

4. [A method of treating pain in a patient in need thereof, said method comprising administering to the patient a medicament comprising an effective amount of an analgesic which is selected from the group consisting of:

2-[4-(3-fluorobenzyloxy)benzylamino]-2-methyl-propanamide;

2-[4-(3-fluorobenzyloxy)benzylamino]propanamide;

2-(4-benzyloxybenzylamino)propanamide;

2-[4-(2-fluorobenzyloxy)benzylamino]propanamide;

2-[4-(4-fluorobenzyloxy)benzylamino]propanamide;

2-[4-(2-chlorobenzyloxy)benzylamino]propanamide;
2-[4-(3-chlorobenzyloxy)benzylamino]propanamide;
2-[4-(3-fluorobenzyloxy)benzylamino]-3-hydroxy-N-methylpropanamide;
2-[4-(2-fluorobenzyloxy)benzylamino]-3-hydroxy-N-methylpropanamide;
2-[4-(2-chlorobenzyloxy)benzylamino]-3-hydroxy-N-methylpropanamide;
2-[4-(3-cyanobenzyloxy)benzylamino]-3-hydroxy-N-methylpropanamide;
2-[4-(3-chlorobenzyloxy)phenylethylamino]-propanamide;
2-(4-benzyloxybenzylamino)-3-hydroxy-N-methyl-propanamide;
2-[4-(2-thenyloxy)benzylamino]-propanamide;
2-[4-(3-fluorobenzyloxy)benzylamino]-N-methylpropanamide;
2-[4-(3-fluorobenzyloxy)benzylamino]-3-hydroxy-propanamide;
2-[4-(2-(3-fluorophenyl)ethyloxy)benzylamino]-propanamide;
2-[4-(2-(3-fluorophenyl)ethyl)benzylamino]-propanamide;
2-[N-4-benzyloxybenzyl-N-methyl-amino]-propanamide;
2-[2-(4-(3-chlorobenzyloxy)phenylethyl)amino]-propanamide;
2-[4-benzylthiobenzylamino]-propanamide;
2-[4-(3-phenylpropyloxy)benzylamino]-propanamide;
2-[4-(4-phenylbutyloxy)benzylamino]-propanamide;
2-[4-(5-phylpentyloxy)benzylamino]-propanamide;
2-[4-benzyloxybenzylamino]-3-phenyl-N-methylpropanamide;
2-[4-benzyloxybenzylamino]-3-methyl-N-methylbutanamide, isomers, mixtures and pharmaceutically acceptable salts]

*The method of claim 1 or claim 6 in which the alpha-aminoamide compound is selected from the group consisting of:*

*2-[4-(2-fluorobenzyloxy)benzylamino]propanamide and individual optical isomers and pharmaceutically acceptable salts* thereof.

5. A pharmaceutical composition [having analgesic activity,] comprising a pharmaceutically acceptable excipient and[, as an active agent,] a compound as defined in [claim 1] *claim 9*.

6. A method of treating *acute or chronic* pain in a patient in need thereof, said method comprising administering to [the] *a* patient *in need of such treatment* an *analgesically* effective amount of an alpha-aminoamide compound of formula (I), (I)

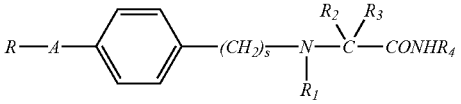

or a pharmaceutically acceptable salt thereof, *wherein:*

*A is a* $—(CH_2)_m—$, $—(CH_2)_n—X—$ *or* $—(CH_2)_v—O—$ *group wherein m is an integer of 1 to 4, n is zero or an integer of 1 to 4, X is —S— or —NH—, and v is zero or an integer of 1 to 5;*

*s is 1 or 2;*

*R is a phenyl ring optionally substituted by one or two substituents independently selected from halogen, cyano,* $C_1$-$C_4$ *alkyl,* $C_1$-$C_4$ *alkoxy and trifluoromethyl;*

$R_1$ *is hydrogen or* $C_1$-$C_4$ *alkyl;*

*one of* $R_2$ *and* $R_3$ *is hydrogen and the other is hydrogen or* $C_1$-$C_4$ *alkyl optionally substituted by hydroxy or phenyl; or* $R_2$ *and* $R_3$ *taken together with the carbon atom to which they are linked form a* $C_3$-$C_6$ *cycloalkyl ring; or* $R_2$ *and* $R_3$ *are both methyl;*

$R_4$ *is hydrogen or* $C_1$-$C_4$ *alkyl,*

*with the proviso that when A is a* $—(CH_2)_5—O—$ *group then s is 1, R is a phenyl group optionally substituted by one or two substituents selected independently from halogen, trifluoromethyl and* $C_1$-$C_4$ *alkoxy,* $R_1$ *is hydrogen and one of* $R_2$ *and* $R_3$ *is hydrogen and the other is hydrogen or* $C_1$-$C_4$ *alkyl optionally substituted by hydroxy.*

7. A compound which is an alpha-aminoamide of formula (IA)

(IA)

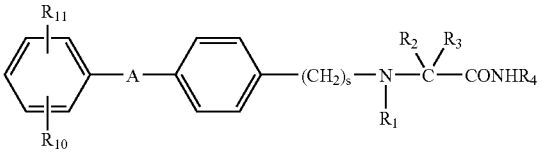

wherein:

A is a $—(CH_2)_m—$ or $—(CH_2)_n—E—$ group wherein m is an integer of 1 to 4, n is zero or an integer of 1 to 4 and E is —O—, —S— or —NH—;

s is 1 or 2;

one of $R_{10}$ and $R_{11}$ is cyano and the other is independently selected from hydrogen, halogen, cyano, $C_1$-$C_4$ alkyl, $C_1$-$C_4$ alkoxy and trifluoromethyl;

$R_1$ is hydrogen or $C_1$-$C_4$ alkyl;

one of $R_2$ and $R_3$ is hydrogen and the other is hydrogen or $C_1$-$C_4$ alkyl optionally substituted by hydroxy or phenyl; or $R_2$ and $R_3$ taken together with the carbon atom to which they are linked form a $C_3$-$C_6$ cycloalkyl ring; or $R_2$ and $R_3$ are both methyl;

$R_4$ is hydrogen or $C_1$-$C_4$ alkyl ring; or a pharmaceutically acceptable salt thereof.

8. A compound according to claim 7, wherein

A is a group $—CH_2—O—$ or $—CH_2—CH_2—O—$, s is 1;

one of $R_{10}$ and $R_{11}$ is cyano and the other is hydrogen, cyano or halogen; and one of $R_2$ and $R_3$ is hydrogen and the other is $C_1$-$C_4$ alkyl optionally substituted by hydroxy; or $R_2$ and $R_3$ are both methyl.

9. A compound selected from the group consisting of:

[2-[4-(3-cyanobenzyloxy)benzylamino]-3-hydroxy-N-methylpropanamide; and

2-[4-(3 cyanobenzyloxy)benzyl]-2-methyl-amino]-3-hydroxy-N-methyl-propanamide;]

*2-[4-(3-cyanobenzyloxy)benzylamino]-3-hydroxy-N-methylpropanamide; and*

*2-[4-(3 cyanobenzyloxy)benzyl-2-methyl-amino]-3-hydroxy-N-methyl-propanamide;*

*optical* isomers, mixtures and pharmaceutically acceptable salts thereof.

10. A pharmaceutical composition comprising a pharmaceutically acceptable excipient and, as an active agent, a compound as defined in claim 7.

11. A method of treating *acute or chronic* pain in a patient in need thereof, said method comprising administering to

[the] *a* patient *in need of such treatment* an analgesic which comprises an effective amount of the compound according to claim 7 and a pharmaceutically acceptable carrier.

12. A method of treating *acute or chronic* pain in a patient in need thereof, said method comprising administering to [the] *a* patient *in need of such treatment* an effective amount of the compound according to claim 7.

*13. The method of claim 1 or claim 6 in which the alpha-aminoamide compound is selected from the group consisting of:*

*2-[4-(3-fluorobenzyloxy)benzylamino]-2-methylpropanamide;*

*2-[4-(3-fluorobenzyloxy)benzylamino]propanamide;*

*2-(4-benzyloxybenzylamino)propanamide;*

*2-[4-(4-fluorobenzyloxy)benzylamino]propanamide;*

*2-[4-(2-chlorobenzyloxy)benzylamino]propanamide;*

*2-[4-(3-chlorobenzyloxy)benzylamino]propanamide;*

*2-[4-(3-fluorobenzyloxy)benzylamino]-3-hydroxy-N-methylpropanamide;*

*2-[4-(2-fluorobenzyloxy)benzylamino]-3-hydroxy-N-methylpropanamide;*

*2-[4-(2-chlorobenzyloxy)benzylamino]-3-hydroxy-N-methylpropanamide;*

*2-[4-(3-cyanobenzyloxy)benzylamino]-3-hydroxy-N-methylpropanamide;*

*2-[4-(3-chlorobenzyloxy)phenylethylamino]propanamide;*

*2-(4-benzyloxybenzylamino)-3-hydroxy-N-methylpropanamide;*

*2-[4-(3-fluorobenzyloxy)benzylamino]-N-methylpropanamide;*

*2-[4-(3-fluorobenzyloxy)benzylamino]-3-hydroxypropanamide;*

*2-[4-(2-(3-fluorophenyl)ethyloxy)benzylamino]propanamide;*

*2-[4-(2-(3-fluorophenyl)ethyl)benzylamino]propanamide;*

*2-[N-4-benzyloxybenzyl-N-methyl-amino]propanamide;*

*2-[2-(4-(3-chlorobenzyloxy)phenylethyl)amino]propanamide;*

*2-[4-benzylthiobenzylamino]propanamide;*

*2-[4-(3-phenylpropoxy)benzylamino]propanamide;*

*2-[4-(4-phenylbutoxy)benzylamino]propanamide;*

*2-[4-(5-phenylpentoxy)benzylamino]propanamide;*

*2-[4-benzyloxybenzylamino]-3-phenyl-N-methylpropanamide;*

*2-[4-benzyloxybenzylamino]-3-methyl-N-methylbutanamide;*

*and optical isomers, mixtures and pharmaceutically acceptable salts thereof.*

*14. The method of claim 1 or claim 6 in which the alpha-aminoamide compound is selected from the group consisting of:*

*2-[4-(3-fluorobenzyloxy)benzylamino]propanamide*

*and individual optical isomers and pharmaceutically acceptable salts thereof.*

*15. The method of claim 1 or claim 6, wherein the pain is neuropathic pain.*

*16. The method of claim 15, wherein the neuropathic pain is a peripheral neuropathic pain.*

*17. The method of claim 15, wherein the pain is trigeminal neuralgia pain.*

*18. The method of claim 15, wherein the pain is postherpetic neuralgia pain.*

*19. The method of claim 15, wherein the pain is diabetic neuropathy pain.*

*20. The method of claim 15, wherein the pain is radiculopathy pain.*

*21. The method of claim 15, wherein the pain is glossopharyngeal neuralgia pain.*

*22. The method of claim 15, wherein the pain is neuropathic pain secondary to metastatic infiltration.*

*23. The method of claim 1 or claim 6, wherein the pain is burn pain.*

*24. The method of claim 1 or claim 6, wherein the pain is chronic pain.*

*25. The method of claim 1 or claim 6, wherein the pain is inflammatory pain.*

*26. The method of claim 1 or claim 6, wherein the pain is adiposis dolorosa pain.*

*27. The method of claim 1 or claim 6, wherein the pain is post-stroke central pain.*

*28. The method of claim 1 or claim 6, wherein the pain is thalamic lesion pain.*

*29. The method of claim 1 or claim 6, wherein the pain is multiple sclerosis pain.*

*30. The method of claim 1 or claim 6, wherein the pain is acute pain.*

*31. The method of claim 4, wherein the pain is neuropathic pain.*

*32. The method of claim 31, wherein the neuropathic pain is a peripheral neuropathic pain.*

*33. The method of claim 31, wherein the pain is trigeminal neuralgia pain.*

*34. The method of claim 31, wherein the pain is postherpetic neuralgia pain.*

*35. The method of claim 31, wherein the pain is diabetic neuropathy pain.*

*36. The method of claim 31, wherein the pain is radiculopathy pain.*

*37. The method of claim 31, wherein the pain is glossopharyngeal neuralgia pain.*

*38. The method of claim 31, wherein the pain is neuropathic pain secondary to metastatic infiltration.*

*39. The method of claim 4, wherein the pain is burn pain.*

*40. The method of claim 4, wherein the pain is chronic pain.*

*41. The method of claim 4, wherein the pain is inflammatory pain.*

*42. The method of claim 4, wherein the pain is adiposis dolorosa pain.*

*43. The method of claim 4, wherein the pain is post-stroke central pain.*

*44. The method of claim 4, wherein the pain is thalamic lesion pain.*

*45. The method of claim 4, wherein the pain is multiple sclerosis pain.*

*46. The method of claim 4, wherein the pain is acute pain.*

*47. The method of claim 14, wherein the pain is neuropathic pain.*

*48. The method of claim 47, wherein the neuropathic pain is a peripheral neuropathic pain.*

*49. The method of claim 47, wherein the pain is trigeminal neuralgia pain.*

*50. The method of claim 47, wherein the pain is postherpetic neuralgia pain.*

*51. The method of claim 47, wherein the pain is diabetic neuropathy pain.*

*52. The method of claim 47, wherein the pain is radiculopathy pain.*

*53. The method of claim 47, wherein the pain is glossopharyngeal neuralgia pain.*

*54. The method of claim 47, wherein the pain is neuropathic pain secondary to metastatic infiltration.*

*55. The method of claim 14, wherein the pain is burn pain.*

*56. The method of claim 14, wherein the pain is chronic pain.*

*57. The method of claim 14, wherein the pain is inflammatory pain.*

*58. The method of claim 14, wherein the pain is adiposis dolorosa pain.*

*59. The method of claim 14, wherein the pain is post-stroke central pain.*

*60. The method of claim 14, wherein the pain is thalamic lesion pain.*

*61. The method of claim 14, wherein the pain is multiple sclerosis pain.*

*62. The method of claim 14, wherein the pain is acute pain.*

*63. The method of claim 1 or claim 6, wherein the administering is by oral administration.*

*64. The method of claim 63, wherein the administering is by oral administration of a tablet.*

*65. The method of claim 63, wherein the administering is by oral administration of a capsule.*

*66. The method of claim 63, wherein the administering is by oral administration of liquid solution or liquid suspension.*

*67. The method of claim 1 or claim 6, wherein the administering is by parenteral administration.*

*68. The method of claim 67, wherein the parenteral administration is intravenous administration.*

*69. The method of claim 68, wherein the intravenous administration is by intravenous infusion.*

*70. The method of claim 68, wherein the intravenous administration is by intravenous injection.*

*71. The method of claim 67, wherein parenteral administration is by intramuscular injection.*

*72. The method of claim 1 or claim 6, wherein the administering is by rectal administration.*

*73. The method of claim 4, wherein the administering is by oral administration.*

*74. The method of claim 73, wherein the administering is by oral administration of a tablet.*

*75. The method of claim 73, wherein the administering is by oral administration of a capsule.*

*76. The method of claim 73, wherein the administering is by oral administration of liquid solution or liquid suspension.*

*77. The method of claim 4, wherein the administering is by parenteral administration.*

*78. The method of claim 77, wherein parenteral administration is intravenous administration.*

*79. The method of claim 78, wherein intravenous administration is by intravenous infusion.*

*80. The method of claim 78, wherein intravenous administration is by intravenous injection.*

*81. The method of claim 77, wherein parenteral administration is by intramuscular injection.*

*82. The method of claim 4, wherein the administering is by rectal administration.*

*83. The method of claim 14, wherein the administering is by oral administration.*

*84. The method of claim 83, wherein the administering is by oral administration of a tablet.*

*85. The method of claim 83, wherein the administering is by oral administration of a capsule.*

*86. The method of claim 83, wherein the administering is by oral administration of liquid solution or liquid suspension.*

*87. The method of claim 14, wherein the administering is by parenteral administration.*

*88. The method of claim 87, wherein parenteral administration is intravenous administration.*

*89. The method of claim 88, wherein intravenous administration is by intravenous infusion.*

*90. The method of claim 88, wherein intravenous administration is by intravenous injection.*

*91. The method of claim 87, wherein parenteral administration is by intramuscular injection.*

*92. The method of claim 14, wherein the administering is by rectal administration.*

*93. The method of claim 63, wherein 1-500 mg of the alpha-aminoamide compound is administered orally per day.*

*94. The method of claim 63, wherein 500 mg-1000 mg of the alpha-aminoamide compound is administered orally per day.*

*95. The method of claim 63, wherein 1000-1500 mg of the alpha-aminoamide compound is administered orally per day.*

*96. The method of claim 63, wherein 1500-2000 mg of the alpha-aminoamide compound is administered orally per day.*

*97. The method of claim 73, wherein 1-500 mg of the alpha-aminoamide compound is administered orally per day.*

*98. The method of claim 73, wherein 500 mg-1000 mg of the alpha-aminoamide compound is administered orally per day.*

*99. The method of claim 73, wherein 1000-1500 mg of the alpha-aminoamide compound is administered orally per day.*

*100. The method of claim 73, wherein 1500-2000 mg of the alpha-aminoamide compound is administered orally per day.*

*101. The method of claim 1 or claim 6, wherein the pharmaceutically acceptable salt is a methanesulfonate salt.*

*102. The method of claim 4, wherein the pharmaceutically acceptable salt is a methanesulfonate salt.*

*103. The method of claim 14, wherein the pharmaceutically acceptable salt is a methanesulfonate salt.*

*104. The method of claim 4, wherein 2-[4-(2-fluorobenzyloxy)benzylamino]propanamide methanesulfonate is administered orally to a human patient at a dose of 1-2000 mg/day.*

*105. The method of claim 104, wherein 2-[4-(2-fluorobenzyloxy)benzylamino]propanamide methanesulfonate is administered orally to a human patient at a dose of 500-1000 mg/day.*

*106. The method of claim 104, wherein the pain is neuropathic pain.*

*107. The method of claim 105, wherein the pain is neuropathic pain.*

*108. The method of claim 104, wherein the pain is inflammatory pain.*

*109. The method of claim 105, wherein the pain is inflammatory pain.*

*110. The method of claim 104, wherein the pain is chronic pain.*

*111. The method of claim 105, wherein the pain is chronic pain.*

*112. The method of claim 104, wherein the pain is radiculopathy pain.*

*113. The method of claim 105, wherein the pain is radiculopathy pain.*

* * * * *